US 7,486,767 B2

(12) United States Patent
Sonobe et al.

(10) Patent No.: US 7,486,767 B2
(45) Date of Patent: Feb. 3, 2009

(54) X-RAY APPARATUS

(75) Inventors: Kouichi Sonobe, Kyoto (JP); Masanori Otsuka, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 238 days.

(21) Appl. No.: 11/208,325

(22) Filed: Aug. 19, 2005

(65) Prior Publication Data

US 2006/0056594 A1    Mar. 16, 2006

(30) Foreign Application Priority Data

Aug. 27, 2004    (JP) .............................. 2004-248955

(51) Int. Cl.
*A61B 6/14*    (2006.01)
(52) U.S. Cl. .......................... 378/39; 378/191; 378/197
(58) Field of Classification Search .................. 378/39, 378/191, 197
See application file for complete search history.

(56) References Cited

U.S. PATENT DOCUMENTS

| | | | | |
|---|---|---|---|---|
| 3,822,875 | A * | 7/1974 | Schmedemann | 5/601 |
| 4,002,915 | A * | 1/1977 | Weiss et al. | 378/39 |
| 4,084,094 | A * | 4/1978 | Froggatt | 378/10 |
| 4,599,739 | A * | 7/1986 | Nishikawa et al. | 378/39 |
| 4,661,967 | A * | 4/1987 | Nishikawa | 378/39 |
| 4,829,549 | A * | 5/1989 | Vogel et al. | 378/55 |
| 4,856,038 | A * | 8/1989 | Guenther et al. | 378/39 |
| 4,907,251 | A * | 3/1990 | Mork et al. | 378/39 |
| 4,969,170 | A * | 11/1990 | Kikuchi et al. | 378/91 |
| 4,987,583 | A * | 1/1991 | Travanty et al. | 378/91 |
| 5,056,365 | A | 10/1991 | Gray et al. | |
| 5,097,495 | A * | 3/1992 | Gray et al. | 378/117 |
| 5,105,455 | A * | 4/1992 | Kato et al. | 378/117 |
| 5,355,398 | A * | 10/1994 | Nakano et al. | 378/39 |
| 5,485,502 | A | 1/1996 | Hinton et al. | |
| 5,651,044 | A * | 7/1997 | Klotz et al. | 378/117 |
| 5,762,608 | A * | 6/1998 | Warne et al. | 600/425 |

(Continued)

FOREIGN PATENT DOCUMENTS

JP            51-86690          7/1976

(Continued)

*Primary Examiner*—Edward J Glick
*Assistant Examiner*—Thomas R Artman
(74) *Attorney, Agent, or Firm*—William L. Androlia; H. Henry Koda

(57) ABSTRACT

One of the aspects of the present invention is to provide an X-ray apparatus, which includes an X-ray source radiating an X-ray to a target portion of a person being tested, an X-ray detector detecting the X-ray through the target portion, and a moving mechanism supporting the X-ray source and the X-ray detector so as to oppose to each other. It also includes a driving mechanism driving said moving mechanism so as to keep said X-ray source and said X-ray detector opposing to each other with the target portion intervened therebetween, while the X-ray source radiates the X-ray, and a drive change detector for detecting a drive change of the driving mechanism to determine whether the moving mechanism is applied with an external force preventing motion of the moving mechanism. The driving mechanism is terminated to drive the moving mechanism when the drive change detector detects that the moving mechanism is applied with the external force preventing motion of the moving mechanism.

8 Claims, 18 Drawing Sheets

U.S. PATENT DOCUMENTS

| | | |
|---|---|---|
| 6,169,780 B1 | 1/2001 | Yoshimura et al. |
| 6,412,978 B1 * | 7/2002 | Watanabe et al. ........... 378/197 |
| 6,430,259 B2 * | 8/2002 | Meek et al. ................. 378/117 |
| 6,470,069 B1 * | 10/2002 | Muller ........................ 378/21 |
| 6,496,558 B2 * | 12/2002 | Graumann ................... 378/39 |
| 6,574,500 B2 * | 6/2003 | Keren ......................... 600/431 |

FOREIGN PATENT DOCUMENTS

| | | |
|---|---|---|
| JP | 64-33605 | 2/1989 |
| JP | 1-17298 | 5/1989 |
| JP | 02-97297 | 4/1990 |
| JP | 6-278082 | 10/1994 |
| JP | 8-19534 | 1/1996 |
| JP | 8-257023 | 10/1996 |
| JP | 11-104124 | 4/1999 |
| JP | 2002-017718 | 1/2002 |
| JP | 2003-174786 | 6/2003 |
| JP | 2003-192153 | 7/2003 |

* cited by examiner

X-RAY APPARATUS

BACKGROUND OF THE INVENTION

1) Technical Field of the Invention

The present invention relates to an X-ray apparatus.

2) Description of Related Arts

Various types of X-ray apparatuses have been developed so far, including for example, a dental panoramic X-ray apparatus disclosed in the U.S. Pat. No. 6,169,780 B1, which includes an X-ray source for radiating X-ray onto the target portion of the person being tested, X-ray detecting means for detecting the X-ray penetrating through the target portion, and supporting means (revolving arm) for movably supporting the X-ray source and the X-ray detecting means so as to oppose each other. In the panoramic X-ray apparatus, the target portion of the person being tested is seated between the X-ray source and the X-ray detecting means opposing thereto, and the revolving arm revolves around the person being tested.

However, the panoramic X-ray apparatus has a drawback, that is, when an external force is applied to the revolving arm during revolution, the moving rate of the X-ray against the target portion varies thereby to cause distortion on an X-ray image. Such a distorted X-ray image cannot be used for diagnosis in practice, and to be worse, the person being tested is exposed with X-ray for nothing.

Another X-ray imaging apparatus disclosed in the U.S. Pat. No. 5,056,365, also includes an X-ray source for radiating the X-ray onto the target portion of the person being tested, X-ray detecting means for detecting the X-ray penetrating through the target portion, and supporting means (revolving arm) for movably supporting the X-ray source and the X-ray detecting means so as to oppose each other. The X-ray apparatus also is provided with a collision sensor having a movable ring member on the X-ray detecting means (receiving apparatus), and the motion of the X-ray detecting means is automatically interrupted when the ring member of the collision sensor contacts a clog.

Also, the X-ray imaging apparatus has several problems, for example, it requires the collision detection moving member to be arranged on the X-ray detecting member, in which smudge can be piled up, thereby preventing sanitation and causing disfigurement thereof. Further, the motion of the X-ray detecting means may be halted just by slight touch thereon of the practitioner and/or the person being tested, and provision of the movable member requires more space for the X-ray imaging apparatus, preventing effective usage of the space.

It should be noted that the aforementioned application are incorporated herein by reference into the present application.

SUMMARY OF THE INVENTION

One of the aspects of the present invention is to provide an X-ray apparatus, which includes an X-ray source radiating an X-ray to a target portion of a person being tested, an X-ray detector detecting the X-ray through the target portion, and a moving mechanism supporting the X-ray source and the X-ray detector so as to oppose to each other. It also includes a driving mechanism driving said moving mechanism so as to keep said X-ray source and said X-ray detector opposing to each other with the target portion intervened therebetween, while the X-ray source radiates the X-ray, and a drive change detector for detecting a drive change of the driving mechanism to determine whether the moving mechanism is applied with an external force preventing motion of the moving mechanism. The driving mechanism is terminated to drive the moving mechanism when the drive change detector detects that the moving mechanism is applied with the external force preventing motion of the moving mechanism.

Preferably, the X-ray source is terminated to radiate the X-ray when the drive change detector detects that the moving mechanism is applied with the external force preventing motion of the moving mechanism.

Preferably, the moving mechanism including a revolving member revolving around a revolution axis and supporting the X-ray source and the X-ray detector so as to oppose to each other, and the driving mechanism including a revolution driver for revolving the revolving member and a translation driver for translating the revolution axis. Also, at least one of revolution by the revolution driver and translation by the translation driver is terminated when the drive change detector detects that the moving mechanism is applied with the external force preventing motion of the moving mechanism.

Further, the drive change detector detects an amount of the drive change of the driving mechanism, and determines that the moving mechanism is applied with the external force preventing motion of the moving mechanism, when the amount of the drive change is beyond a predetermined range of threshold values.

In addition, the X-ray apparatus includes a clock pulse generator for generating clock pulse signals. The drive change detector detects clock pulse signals in ON/OFF durations which appear alternately and synchronously with the driving of the driving mechanism so as to detect the amount of the drive change of the driving mechanism.

Preferably, the drive change detector detects the drive change of the driving mechanism by detecting motion of the moving member which synchronously moves with the driving mechanism.

In particular, the driving mechanism includes a revolution driver for revolving the moving mechanism at a revolution rate, and the drive change detector includes a rate sensor for detecting the revolution rate so as to determine that the moving mechanism is applied with the external force preventing motion of the moving mechanism, when the revolution rate is reduced less than a predetermined threshold revolution rate.

Alternatively, the driving mechanism includes a revolution driver for revolving the moving mechanism with a rotation torque, and the drive change detector including a torque sensor for sensing the rotation torque applied to the revolution driver so as to determine that the moving mechanism is applied with the external force preventing motion of the moving mechanism, when the rotation torque is beyond a predetermined range of threshold values.

Also, the drive change detector includes one of a group consisting of an optical sensor, laser sensor, infra-red sensor, magnetic sensor, semiconductor magnetic sensor, and magnetic proximity sensor.

Further scope of applicability of the present invention will become apparent from the detailed description given herein. However it should be understood that the detailed description and specific examples, while indicating preferred embodiments of the invention, are given by way of illustration only, since various changes and modifications within the sprit and scope of the invention will become apparent to those skilled in the art from this detailed description.

BRIEF DESCRIPTION OF THE DRAWINGS

The present invention more fully be understood from the detailed description given herein and accompanying drawings which are given by way of illustration only, and thus are not limitative of the present invention.

DETAILED DESCRIPTION OF THE PREFERRED EMBODIMENTS

Figure 1:
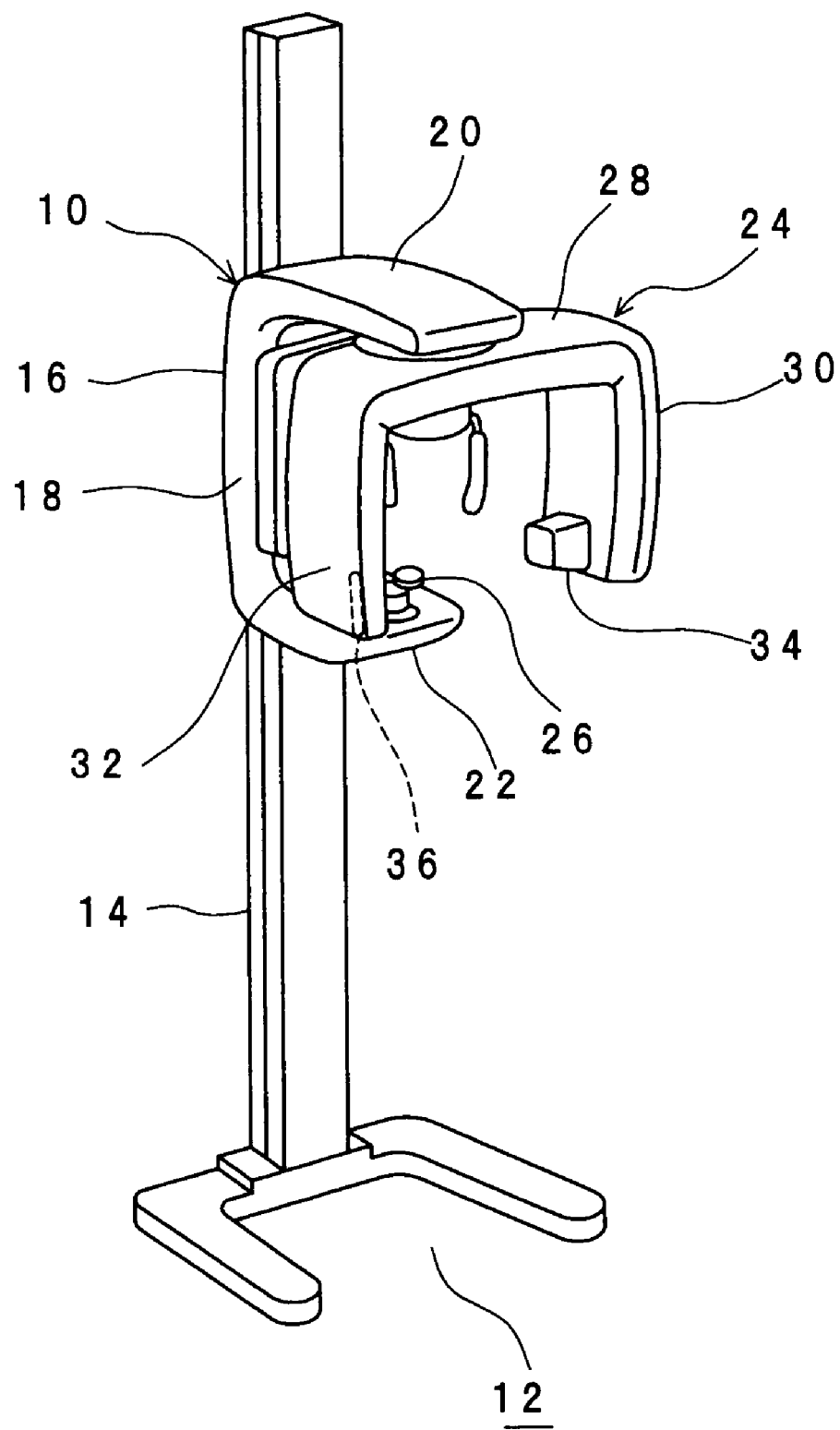
FIG. 1 is a perspective view of the X-ray apparatus according to the first embodiment of the present invention.

Referring to the attached drawings, the details of embodiments according to the present invention will be described herein. In those descriptions, although the terminology indicating the directions (for example, "upper", "lower", "upwardly", and "downwardly") is conveniently used just for clarity, it should not be interpreted that those terminology limit the scope of the present invention. Also, the components commonly used in the following embodiments have the same reference numerals through the present application, and the duplicate description for the similar structure of the embodiments will be eliminated.

Further, in the context of the present application, various moving components/elements that move (rotate, revolve, and translate) and driving components/elements for driving the moving components/elements may collectively be referred to as the moving means/mechanism and driving means/mechanism, respectively.

Embodiment 1

(1) Structure of X-Ray Apparatus

Figure 2:
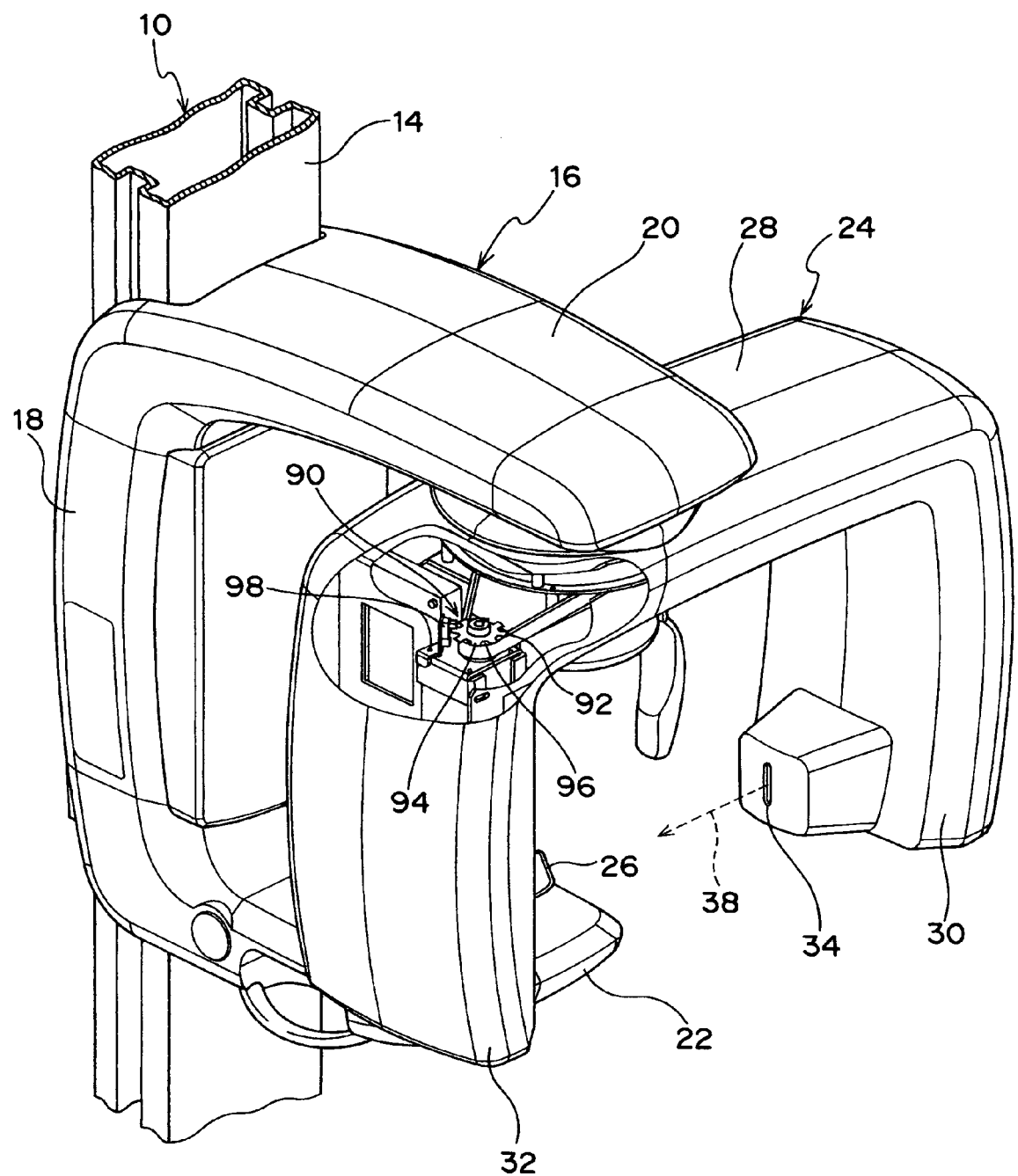
FIG. 2 is a perspective view of the revolving arm incorporated in the X-ray apparatus of FIG. 1.
Figure 3:
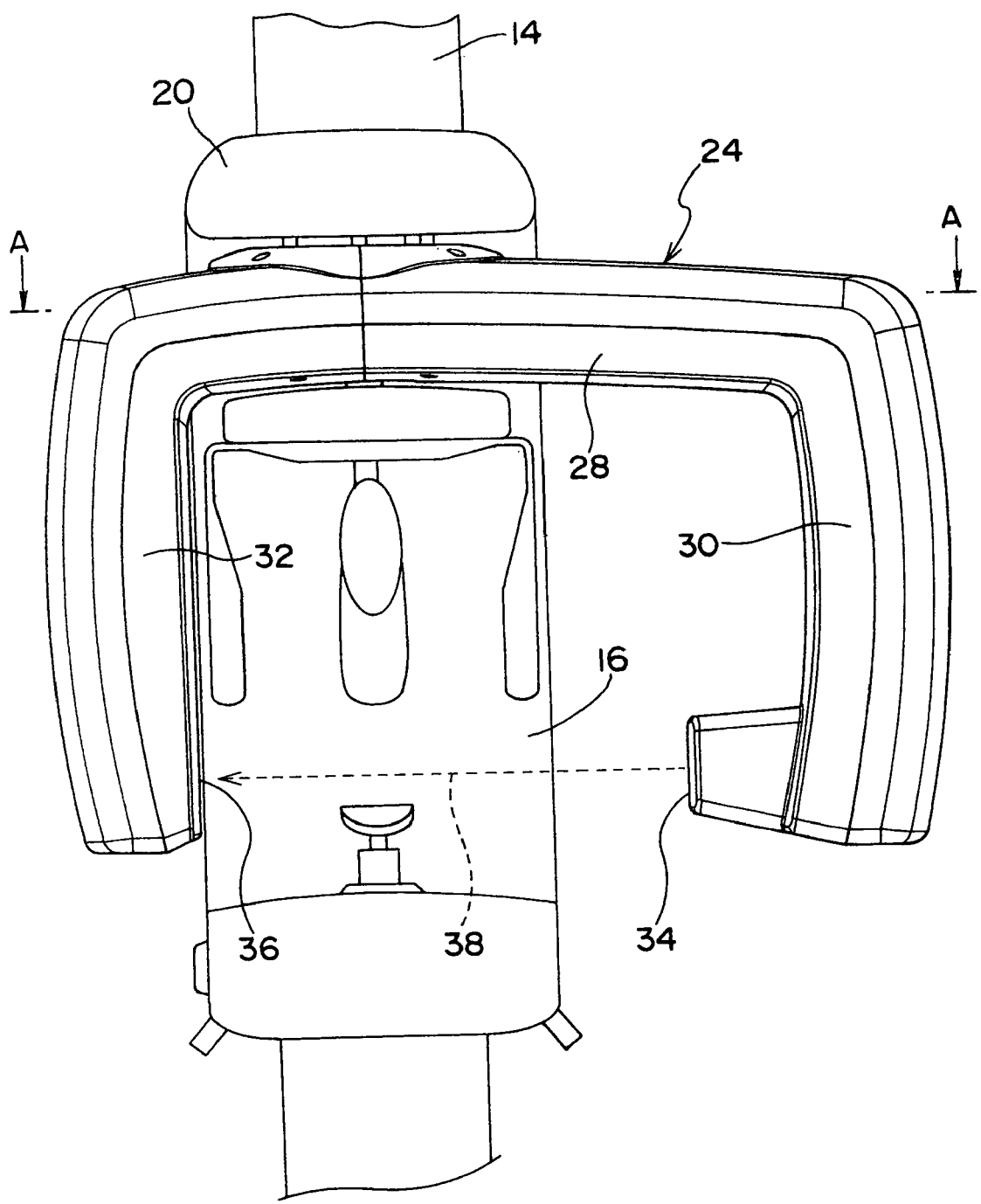
FIG. 3 is a side view of the revolving arm incorporated in the X-ray apparatus of FIG. 1.

FIG. 1 illustrates an X-ray apparatus 10 according to the present invention. As shown, the X-ray apparatus 10 includes a column 14 secured on the floor 12. The column 14 slidably supports a U-shaped vertical member 16 capable of moving upwardly and downwardly. The vertical member 16 includes a main body 18, and upper and lower frames 20, 22 which extend forwardly from upper and lower ends of the main body 18, respectively. Also, the upper frame 20 supports a revolving arm (moving mechanism) 24 beneath the upper arm 20, and the lower frame 22 supports a seating station 26 for fixing a target portion (e.g., the head) of the person (object) being tested. As illustrated in FIGS. 2 and 3, the revolving arm 24 includes a horizontal portion 28 and a pair of suspending portions 30, 32 suspending from the ends of the horizontal portion 28, and is designed such that it can revolve and/or move along with revolution around the vertical axis (revolution axis, not shown herein), which will be described below in detail. An X-ray source 34 is provided on one of the suspending members 30, and an X-ray detector (detecting means) 36 is arranged on the other one of the suspending members 32. According to the X-ray apparatus 10 so structured, the target portion of the person being tested (or a patient) is seated on the seating station 26 and between the suspending portions 30, 32 opposing to each other, and is exposed, from various angles, with the X-ray 38 radiated from the X-ray source 34 that revolves or moves along with revolution around the patient, so that the X-ray detector 36 detects the X-ray 38 transmitted through the target portion of the patient, thereby producing the pamoramic X-ray image of the target portion of the patient.

(2) Translating and Revolving Mechanism

As will be described herein in detail, the X-ray apparatus 10 includes a translating and revolving mechanism for providing the revolving arm 24 with motion that is combined with revolution around an axis and translation back and forth. The translating and revolving mechanism includes, in general, driving means such as a driving motor and moving means including, for example, a revolving arm driven by the driving motor.

(2-1) Structure of Translating and Revolving Mechanism

Figure 4:
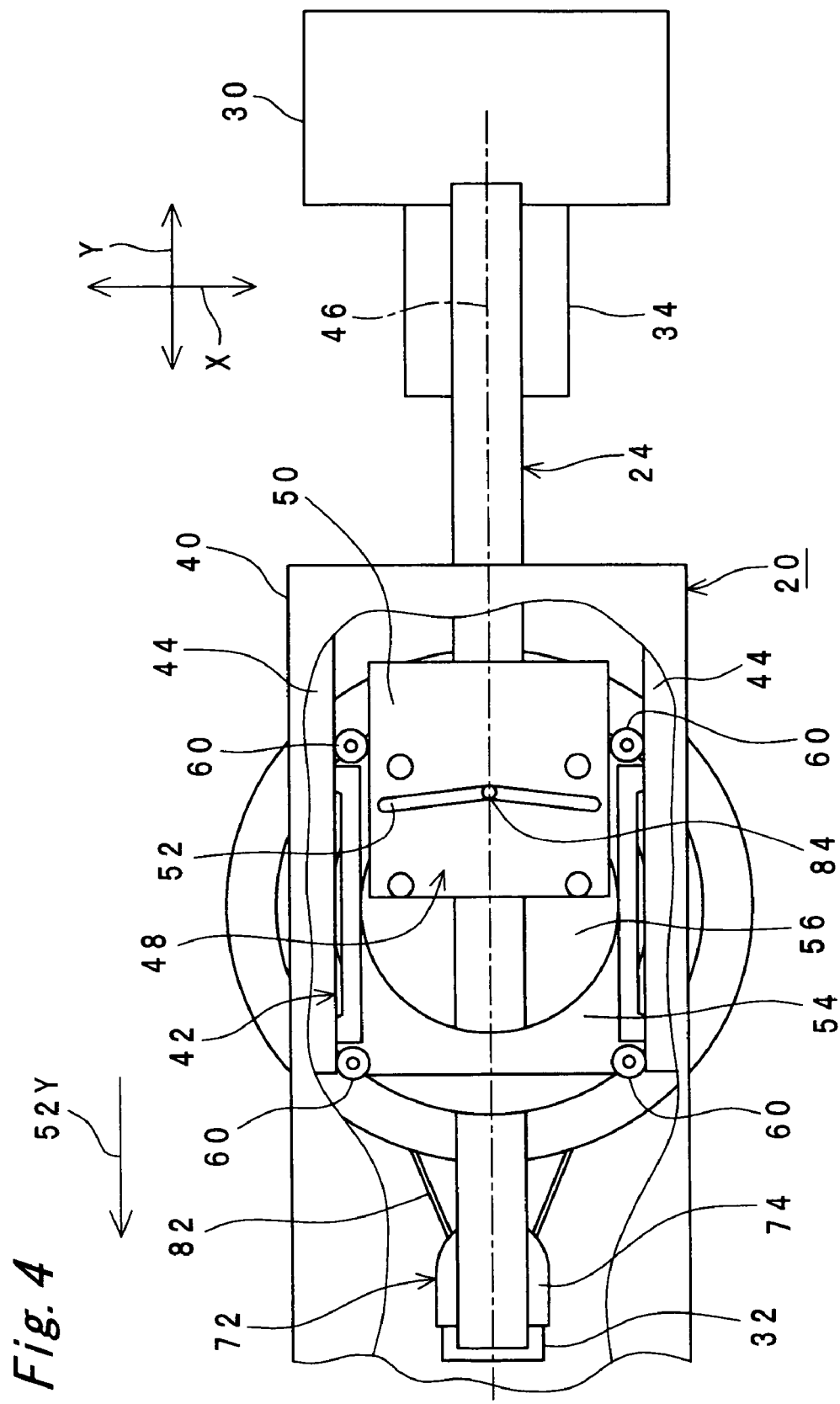
FIG. 4 is a top plane view illustrating the structure of the translating and revolving mechanism adapted for the X-ray apparatus of FIG. 1.
Figure 5:
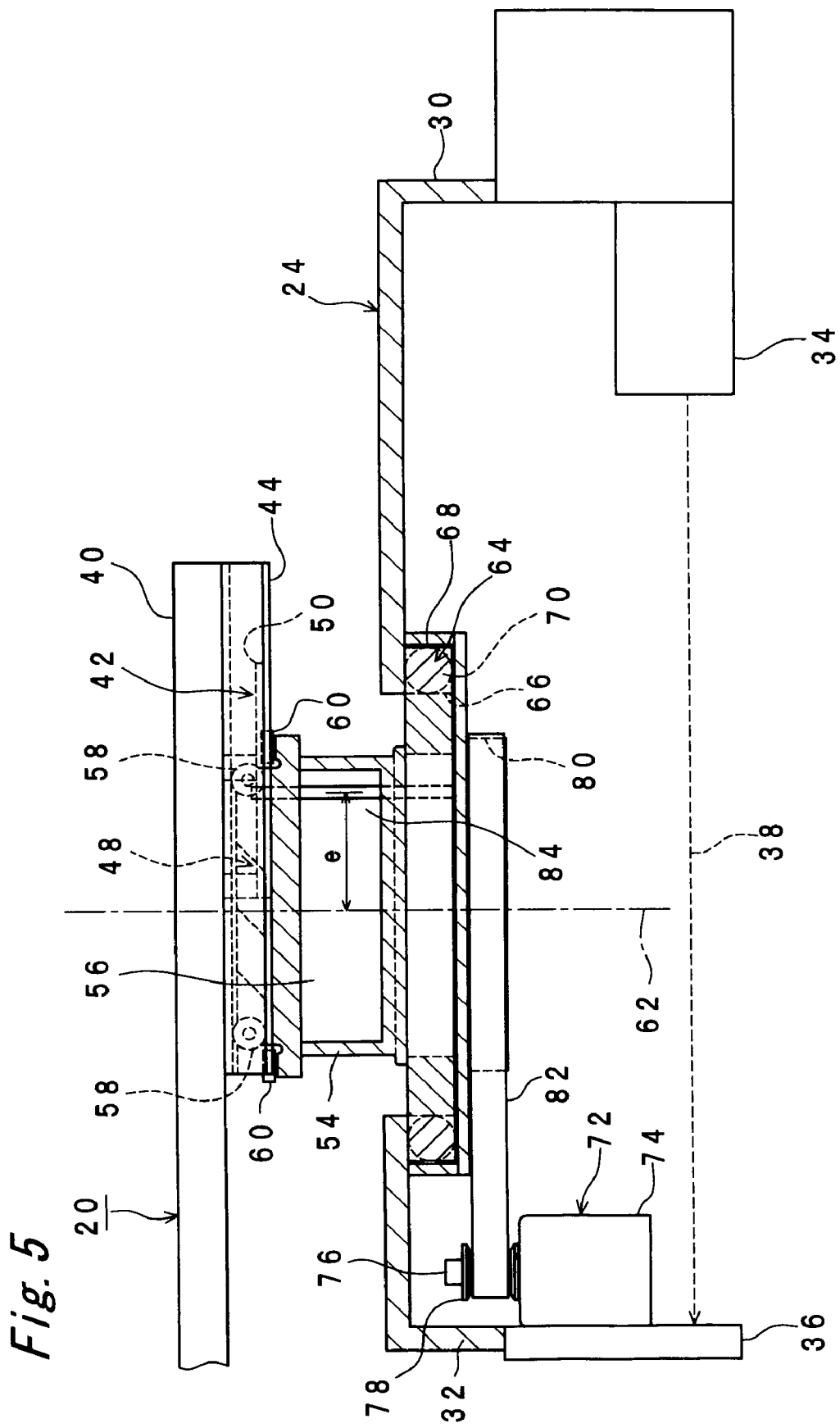
FIG. 5 is a vertical cross section illustrating the structure of the translating and revolving mechanism adapted for the X-ray apparatus of FIG. 1.

As illustrated in FIGS. 4 and 5, the upper frame 20 includes a fixed frame 40 which has a first guide member 42. In the present invention, the first guide member 42 includes a pair of guide rails 44, which are arranged in parallel and symmetrically relative to the horizontal axis (horizontal center) along the horizontal direction (Y-direction of the arrow in FIG. 4), in which the main body 18 of the vertical member 16 opposes the patient. Also, in the present embodiment, the second guide member 48 includes a guide plate 50 horizontally secured between the pair of the guide rails 44. The guide plate 50 has a guide slot (guide channel) 52 extending across the horizontal axis 46 and symmetrically relative to the horizontal axis 46. In the present embodiment, the guide slot 52 has a V-shaped form straightly extending from the horizontal center 46 with an angle along a forward direction as indicated by an arrow in the Y-direction and symmetrically relative to the horizontal center as shown in FIG. 4. Alternatively, both of wings of the V-shaped guide slot 52 may extend with slight curve or arc towards the circumference of the slot, or the V-shaped guide slot 52 may be designed, as a whole, in an arcuate form.

The first guide member 42 supports the translating frame (movable portion) 54 moving in the Y-direction along and between the pair of the guide rails 44. According to the present embodiment, the translating frame 54 has a hollow space 56 extending therethrough in the vertical direction, and includes supporting rollers 58 and transversal limiting rollers 60 formed at four corner of the translating frame 54, in which the transversal limiting rollers 60 limit the motion in the direction transverse to the Y-direction (i.e., the X-direction in FIG. 4) and the supporting rollers 58 allows the motion in the Y-direction in conjunction with rotation of the supporting rollers 58.

The translating frame 54 rotatably supports the revolving arm 24 by means of a bearing 64 arranged around the vertical axis (revolution axis) 62 perpendicular to the horizontal axis 46. In the present embodiment, the bearing 64 may be designed as a roller bearings, including an inner ring 66 formed on the translating frame 54, an outer ring 68 formed on the revolving arm 24, and a plurality of rolling members (beads) 70 provided between the inner ring 66 and the outer ring 68.

The translating frame 54 and/or the revolving arm 24 also includes a driving member 72 for driving the revolving arm 24 relative to the translating frame 54. The driving member 72 has a motor 74 (driving means). In the present embodiment, the motor 74 may be mounted on the revolving arm 24, e.g., the suspending member 32 that also has the X-ray detector 36. Also, a pulley is provided on the rotating shaft 76 of the motor 74. The translating frame 54 includes a cylindrical supporting member (fixed counteraction member) 80 formed along the circumference with its center on the vertical axis 62. A transmission belt (rotating member) 82 is provided over and between the cylindrical supporting member 80 and the pulley 78 for transferring the driving force of the driving member 72 to the cylindrical supporting member.

The revolving arm 24 also includes a vertical rod 84 (guided member) extending upwardly. Thus, the vertical rod 84 stands extending along a vertical plane including a path of the X-ray flux 38 that passes from the X-ray source 34 to the X-ray detector 36. Also, the vertical rod 84 stands extending through the inner space 56 of the translating frame 54, and has an upper end inserted into the guide slot 52 of the guide plate 50. Further, as illustrated, the vertical rod 84 is provided at an eccentric position spaced from the vertical axis 62 by a predetermined distance e.

(2-2) Operation of Translating and Revolving Mechanism

According to the translating and revolving mechanism so structured, upon rotation of the motor 74 of the driving member 72, the rotating force is transmitted from the motor rotating shaft 76 via the pulley 78 to the transmission belt 82. However, since the translating frame 54 is restricted to revolve, the transmission belt 82 is counteracted due to the friction between the translating frame 54 and the cylindrical supporting member 80 so that the revolving arm 24 is driven by the counteraction to revolve around the vertical axis 62. Thus, the motor 74 of the driving member 72 drives the revolving arm 24 of the moving member so as to keep the X-ray source and the X-ray detector opposing to each other with the target portion intervened therebetween, while said X-ray source 34 radiates the X-ray.

As the revolving arm 24 revolves, the vertical rod 84 fixed on the revolving arm 24 moves in and along the guide slot 52. Since the guide slot 52 is not arranged on the circumference with its vertical center 62, revolution of the revolving arm 24 causes the guide slot 52 to push the vertical rod 84 in response to the position of the vertical rod 84 along the Y-direction, so that the translating frame 51 moves along the Y-direction relative to the guide plate 50 and the fixed frame 40. To this result, the revolving arm 24 translates along the Y-direction in conjunction with revolution around the vertical axis 62. That is, the combined motion of translation and revolution (i.e., translating and revolving motion) of the revolving arm 24 can be achieved.

(3) Drive Change Detecting Mechanism

A drive change detecting mechanism (apparatus) will be explained herein, which terminates revolution of the revolving arm 24 and radiation of X-ray once a person being tested (e.g., patient) touches the revolving arm 24 to give an external force preventing revolution thereof.

(3-1) Structure of Drive Change Detecting Mechanism

Figure 6:
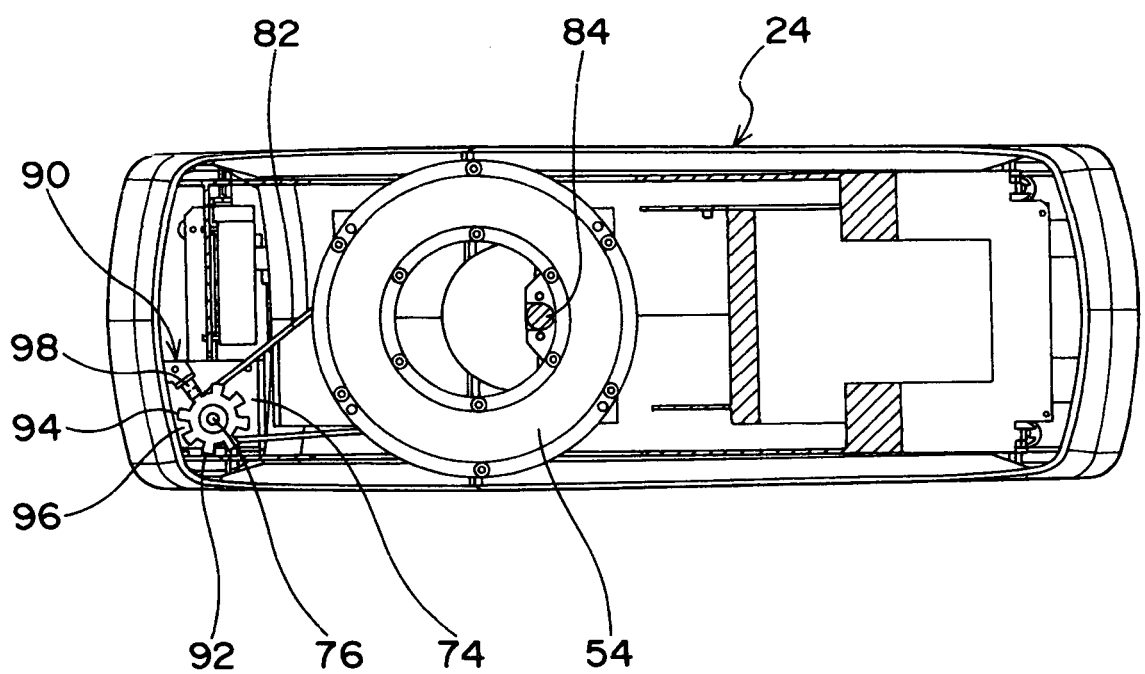
FIG. 6 is a horizontal cross section illustrating the structure of the translating and revolving mechanism adapted for the X-ray apparatus of FIG. 1.
Figure 13:
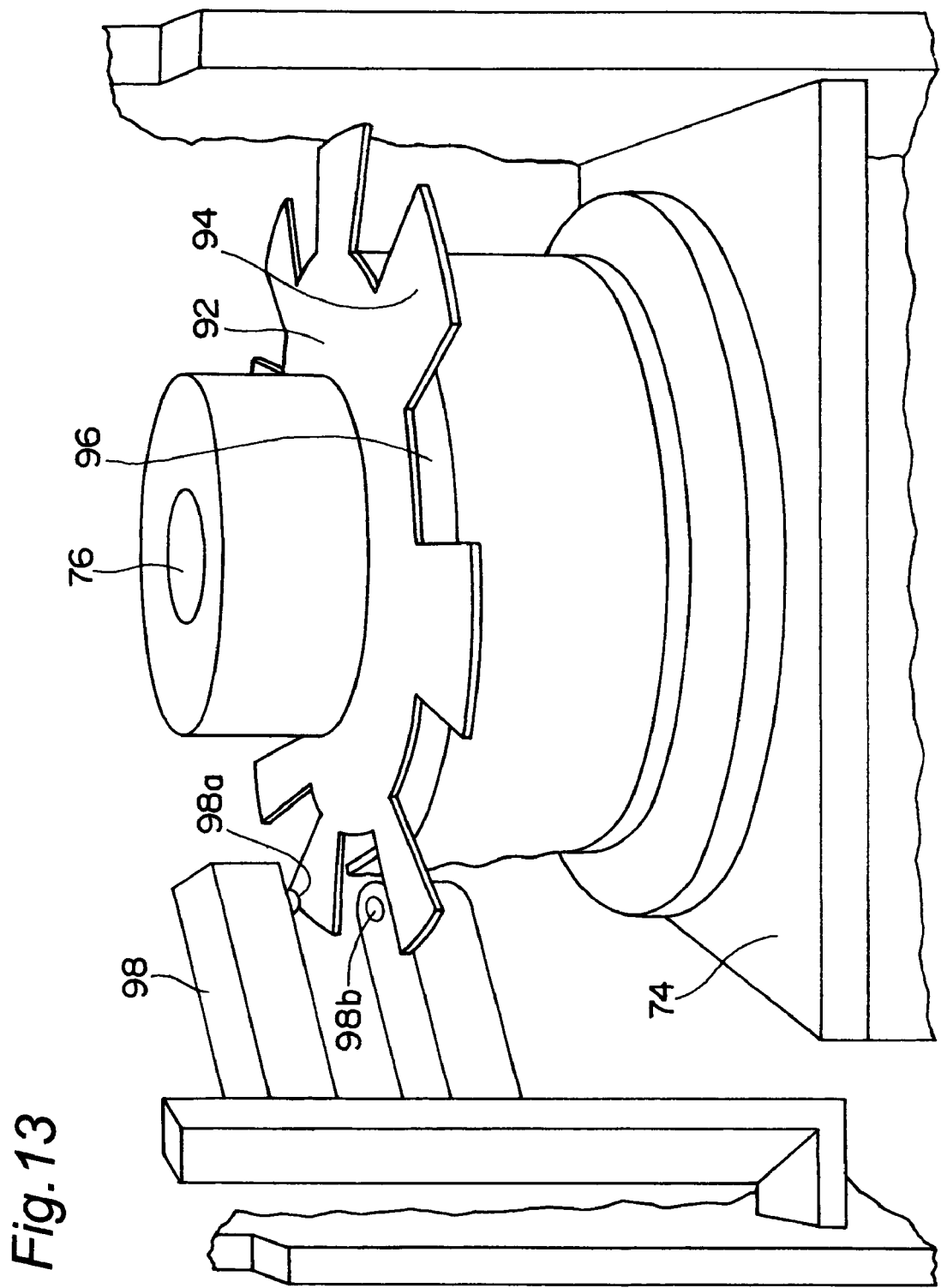
FIG. 13 is an enlarged perspective view of the drive change detecting apparatus.

In FIGS. 2, 6, and 13, the drive change detecting mechanism 90 is provided for detecting an amount of the drive change (e.g., the driving rate) of the moving mechanism such as the motor 74. The drive change detecting mechanism 90 includes a circular light-intercepting plate 92 mounted on the rotating shaft 76 of the motor 74. In the present embodiment, since the circular light-intercepting plate 92 rotates with the rotating shaft 76 of the motor 74, it can be referred to as the synchronous moving member rotating synchronously with the motor 74. However, the circular light-intercepting plate 92 is not always required to be fixed directly onto the rotating shaft 76 of the motor 74. Alternatively, it may be mounted on another rotating shaft (not shown) that is driven by the motor 74 via any transmission means such as a pulley, belt, and gear (not shown), for rotating synchronously with rotation of the motor 74. Also, the circular light-intercepting plate 92 may be driven by the cylindrical supporting member 80. Even in this event, since the circular light-intercepting plate 92 rotates synchronously with the revolving arm 24 revolving in response to the rotating shaft 76 of the motor 74, the circular light-intercepting plate 92 rotates synchronously with the revolving arm 24.

According to present invention, the circular light-intercepting plate 92 includes, as best illustrated in FIG. 13, a plurality of shielding and transmitting portions 94, 96 alternately formed on the circumference of the circular plate by cutting out the shielding portions at a predetermined interval, in which the shielding portion is designed to have the length of the arc (or center angle) same as one of the transmitting portion. The drive change detecting apparatus 90 also includes a photo-interrupter 98 mounted adjacent the circumference of the light-intercepting plate 92. The photo-interrupter 98 consists of a light-emitting element 98a and a light-receiving element 98b, which are configured such that a beam path between the light-emitting element 98a and the light-receiving element 98b is transmitted and interrupted regularly by the light-intercepting plate 92.

(3-2) Control Circuit

Figure 7:
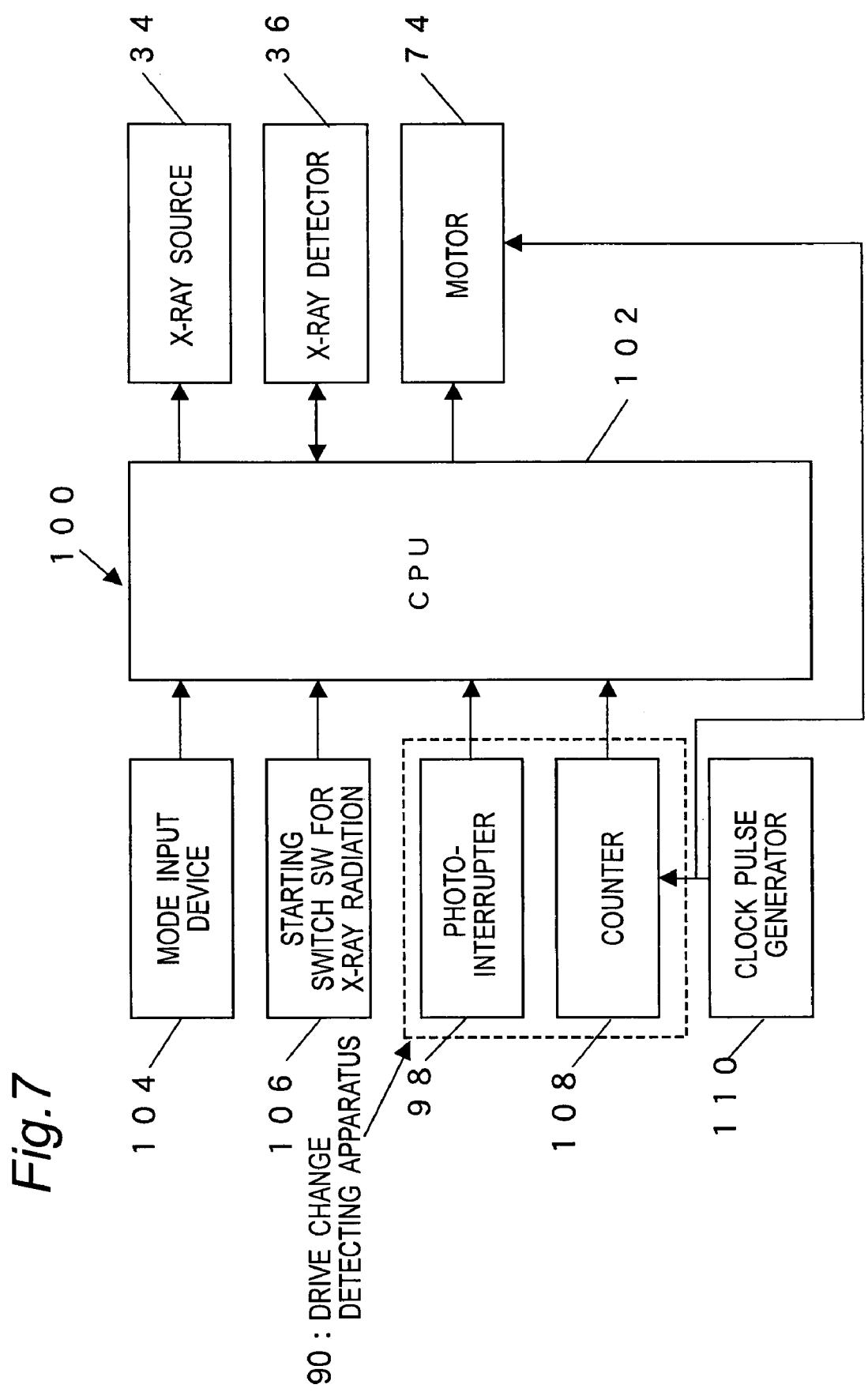
FIG. 7 is a circuit diagram of a control circuit for controlling the drive of the X-ray apparatus.
Figure 9:
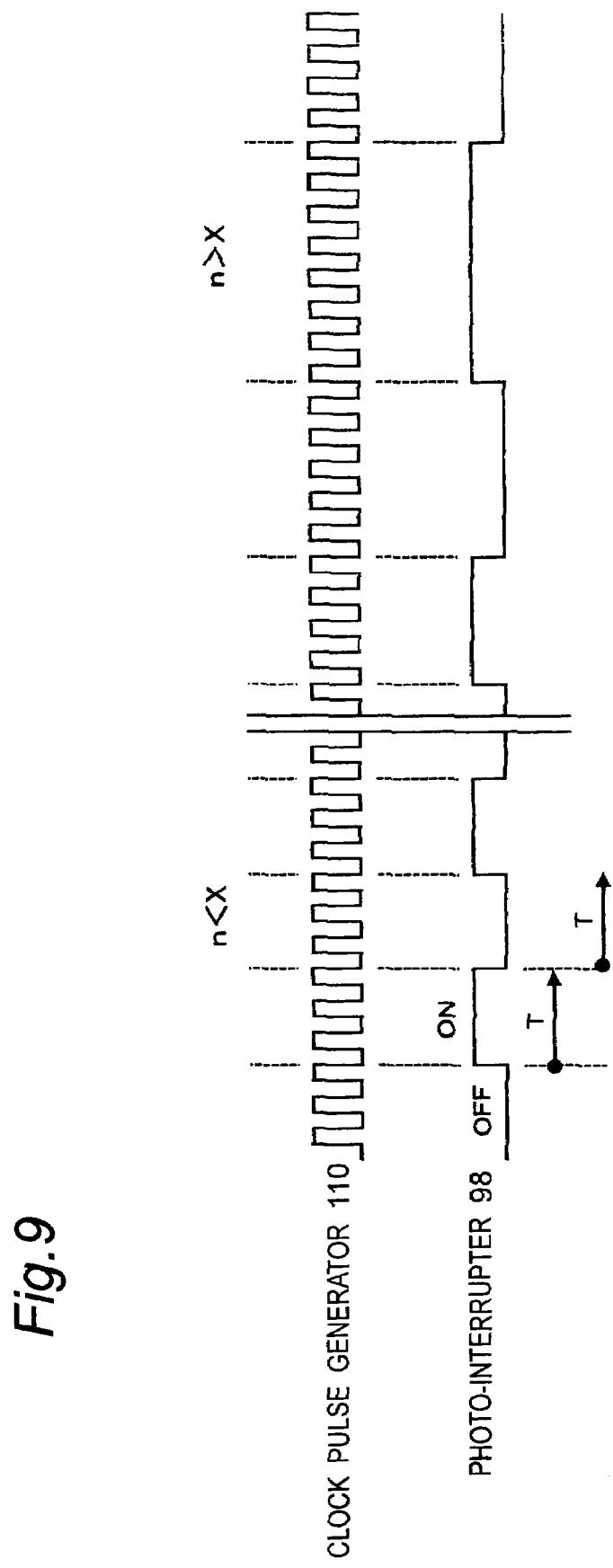
FIG. 9 is a timing chart showing the clock pulse signal output from the clock pulse generator and the ON/OFF-durations, in which the beam pulse of the photo-interrupter is transmitted (output) and intercepted (blocked).

FIG. 7 is a circuit diagram of a control circuit 100 having the drive change detecting apparatus 90 of the X-ray apparatus 10 according to the present embodiment. The control circuit 100 includes a central processing unit 102, which is connected with the X-ray source 34, the X-ray detector 36, and the motor 74. Also, the control circuit 100 is connected with a mode input device 104 provided with a console (not shown), a starting switch 106 for X-ray radiation, and the drive change detecting apparatus 90 having a photo-interrupter 98 and a revolution-failure detecting counter 108. The revolution-failure detecting counter 108 is connected with a clock generator (clock pulse generating means) 110, which generates clock pulses at a given frequency as illustrated in FIG. 9. As shown in FIG. 7, the clock pulse signals generated by the clock generator 110 are supplied with the motor (stepping motor) 74, which precisely controls rotation of the motor 74 with the clock pulse signals. While the clock pulse signals by a general clock pulse generator 110 may be used without modification, any predetermined number of the clock pulses may be combined and used by the drive change detecting apparatus 90 as a single unit of a counting pulse for detecting the drive change in accordance with the present embodiment. For example, the drive change detecting apparatus 90 may count a single pulse when receiving ten clock pulses generated by the clock pulse generator 110. In this design, various timing control can easily be obtained by choosing any desirable number of the clock pulse signals combined to render the single counting pulse. Also, the clock pulse signals are supplied with the light-emitting element 98a of the photo-interrupter 98 emitting the beam signals at the same given frequency which is received by the light receiving element 98b. The circular light-intercepting plate 92 intercepts and transmits the beam signals alternately in OFF-duration (OFF-state) and ON-duration (ON-state), respectively, of which interval varies in response to the rotation rate of the drive means such as the motor 74. In this case, the beam signals has a pattern periodically oscillating as the clock pulse signals generated by the clock pulse generator 110 as illustrated in FIG. 9, and the revolution-failure detecting counter 108 may count the beam signals output from the photo-interrupter 98 in the OFF-duration (through the transmitting portion 96) for determining whether the detected numbers of the beam signals exceeds a threshold counter value n, as will be described herein in detail.

(3-3) Drive Change Detecting Process

Figure 8:
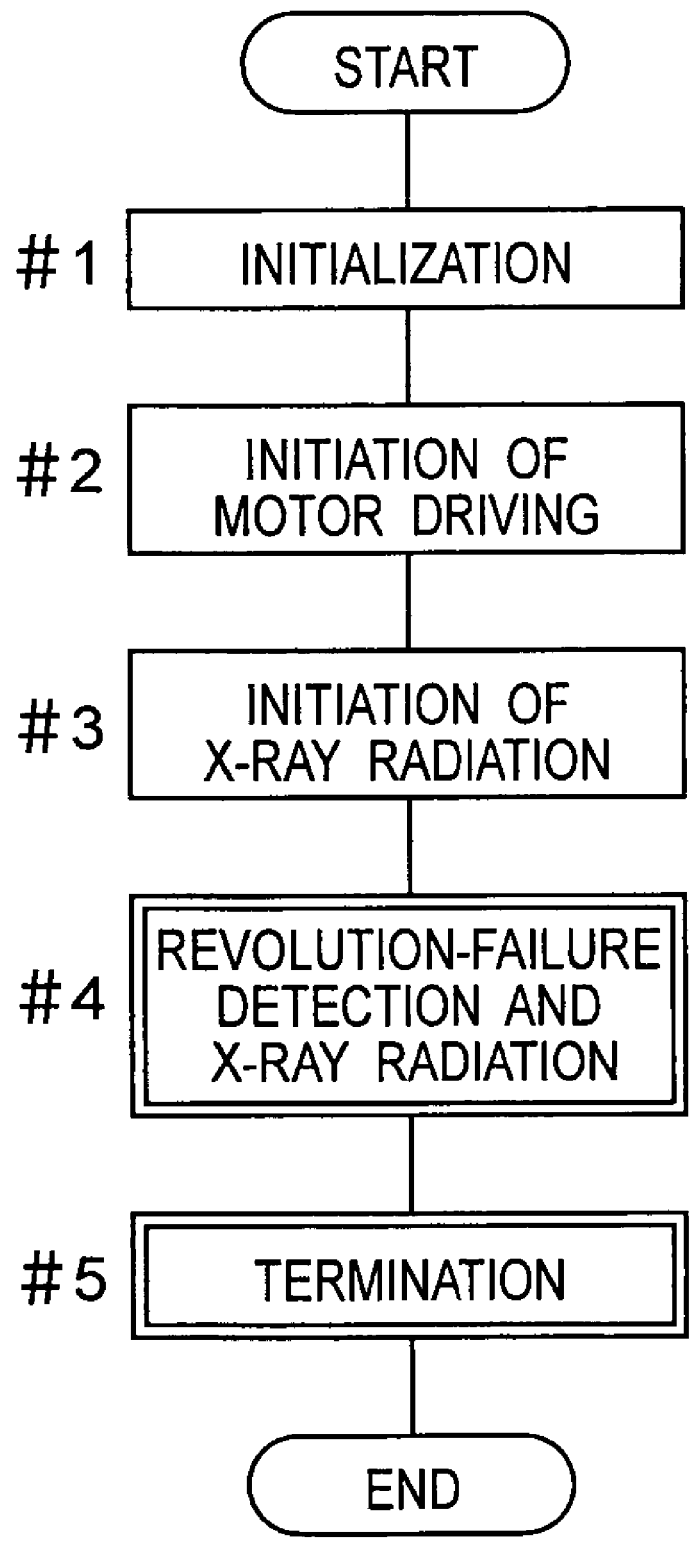
FIG. 8 is a flow chart of the main routine for controlling the drive of the X-ray apparatus.

The detecting process of the drive change with use of the control circuit 100 will be described herein. FIG. 8 is a flowchart illustrating the main routine of the control circuit 100. At Step #1, when a tomography mode (e.g., standard panoramic tomography mode) is selected by means of the mode input device 104 and the starting switch 106 of X-ray radiation is turned on, the central processing unit (CPU) 102 initializes all parameters such as a counter value and flag as default values. The central processing unit 102 drives the motor 74 to move the revolving arm 24 to the tomography starting position appropriate for the selected tomography mode, and to rotate the revolving arm 24 for imaging the tomography. After starting to drive the revolving arm 24 at Step #2, the central processing unit 102 instructs the X-ray source 34 to initiate the X-ray radiation at Step #3. This causes the translating and revolving mechanism to rotate around the central axis 62 and translate the revolving arm 24 back and forth, so that the target portion of the person being tested is exposed with the X-ray flux 38 radiated from the X-ray source 34 and the transmitted X-ray flux 38 through the target portion is detected at the X-ray detector 36 for imaging the X-ray tomography. In the revolving-failure detecting process at Step #4 during imaging the X-ray tomography, the drive change detecting apparatus 90 detects (or counts) the clock pulse signals (beam signals) alternately switching ON and OFF that are output by the photo-interrupter 98 so as to determine whether the revolving arm 24 is effected with the external force preventing the revolution of the revolving arm 24 because, for example, the patient touches the revolving arm 24. As above, the intervals of the ON/OFF-durations of the beam signals output from the photo-interrupter 98 depend upon the rotation rate of the circular light-intercepting plate 92, and thus synchronize with rotation of the driving means.

Figure 10:
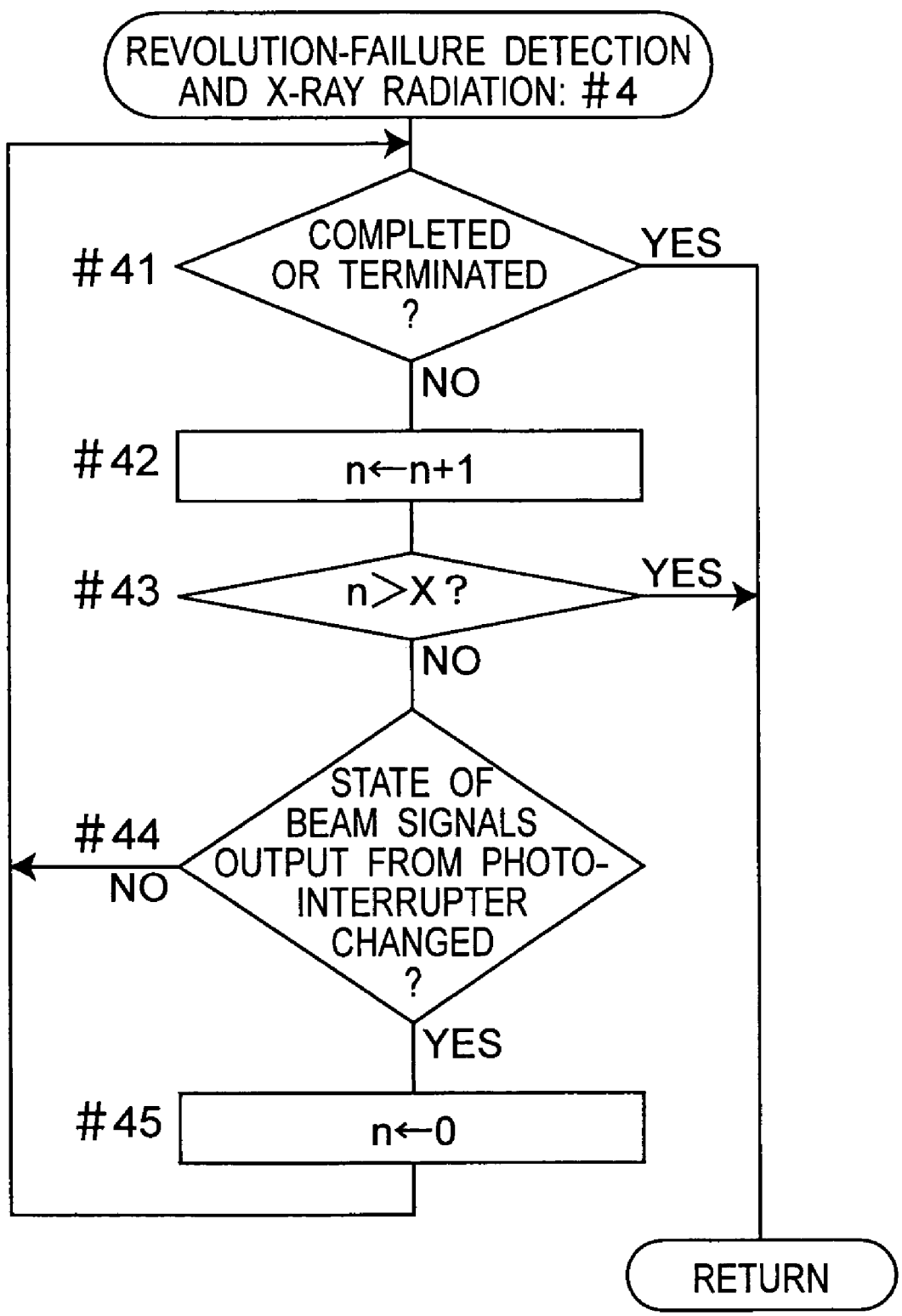
FIG. 10 is a flow chart of the sub-routine for the revolving-failure detecting process.
Figure 11:
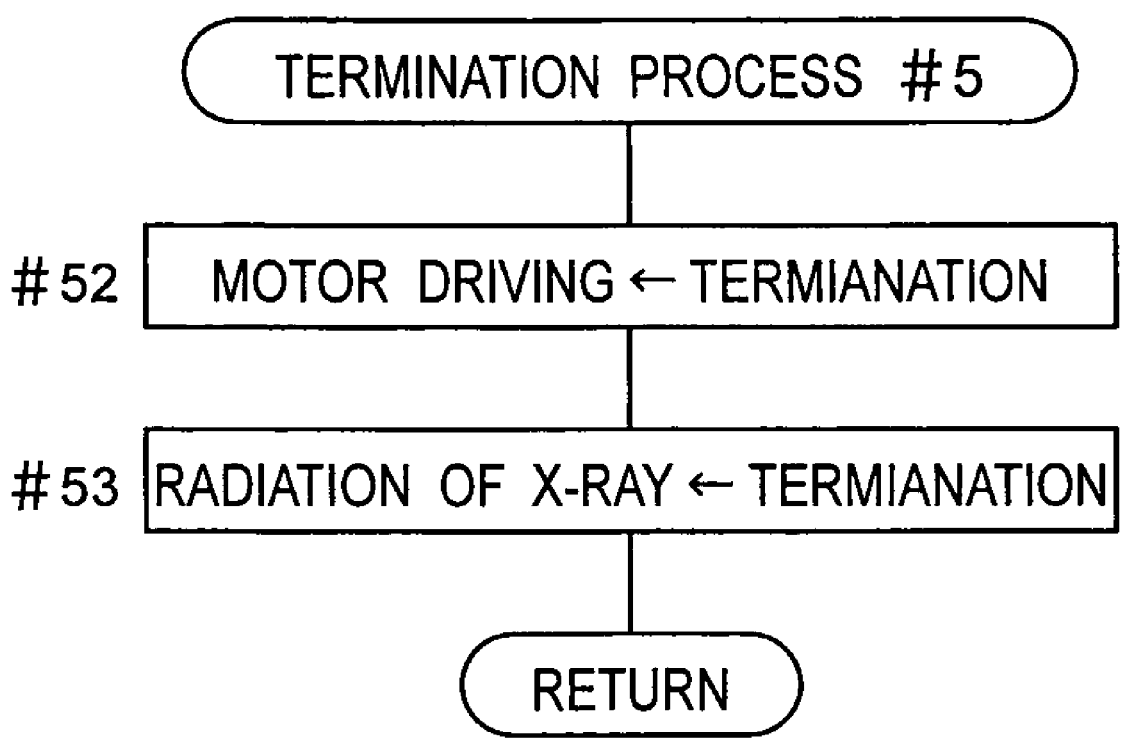
FIG. 11 is a flow chart of the sub-routine for the termination step.

As above, while imaging the X-ray tomography, the pulsed beam signals output from the photo-interrupter 98 in the ON-duration are counted in the revolving failure detecting process at Step #4. In more particular, as shown in FIG. 10, when the X-ray radiation is started, it is determined at Step #41, whether the imaging of the tomography is completed or terminated. When it is completed or terminated, the process is returned to the main routine for the next termination process at Step #5. Meantime, when operation of the tomography is not completed nor terminated, it is forwarded to the counting step at Step #41. While initialization in Step #1 resets the counter value n to zero, the revolution-failure detecting counter 108 increments the counter value n to n+1 at Step #42 upon detecting one of the beam signals (clock pulse signals) output by the photo-interrupter 98. When the motor 74 rotates at the predetermined rotation rate, the same number $X_0$ of the pulsed beam signals output from the photo-interrupter 98 are to be counted in the ON-duration where the circular light-intercepting plate 92 transmits the beam signals. Then, at Step #43, the counter value n is compared with a predetermined threshold value X, which is set to be slightly greater than the number $X_0$ where the pulsed beam signals is counted in the ON-duration at the normal rotation rate of the motor 74 (comparison of the motion). If the counter value n is determined to be not exceeding to (equal or less than) the threshold value X ($n \leq X$; the case of "NO"), then it is determined at Step #44, whether the ON/OFF-states (durations) of the beam signals output from the photo-interrupter 98 has changed, i.e., whether the ON-state transits to the OFF-state or vise versa. If the state has changed (the case of YES), the revolution-failure detecting counter 108 is reset to zero, back to Step #41, and it is determined again whether the operation of the tomography is completed or terminated. When it is completed or terminated, the process is returned to the main routine for the termination process at Step #5. The termination process terminates driving the motor 74 and radiating the X-ray. Meanwhile, if no change of the states (durations) of the beam signals is found, Step #44 moves to Step #41 and the incrementation step of the counter value n is kept going.

On the other hand, if it is so determined that the counter value n is determined to be greater than the threshold value X ($n > X$; the case of "YES") at Step #43, a termination flag is set to be "1 (one)" and the process is returned to the main routine to go to the termination step at Step #5. This corresponds to the case where the revolving arm 24 is effected with the external force preventing the revolution of the revolving arm 24 by, for example, the patient's unintentional touch on the revolving arm 24, so that the ON/OFF-duration defined by the rotation rate of the circular light-intercepting plate 92 is extended and the incremented counter number n of the beam signals output from the photo-interrupter 98 is greater than the predetermined number X. While the termination flag is set to be "0 (zero)" in the initialization, it is used, at Step #5, to determine that abnormal termination (abortion) is made with the termination flag set as "1", and the process is normally terminated when the termination flag is set as "0" after the normal completion of the tomography or the completion with the practitioner's intended terminating operation.

The revolving arm 24 may be rotated at the constant rate or varying rate. Also, the threshold value X may change between initiation and termination of the tomography imaging. For example, in the art of the dental panoramic tomography, it is well known that the revolving arm 24 revolves more slowly to take the tomography image for the anterior teeth because the X-ray is more intensively blocked by the cervical spine, and revolves more quickly for the other portions. As the rotation rate of the motor 74 is slower for the anterior teeth, the ON/OFF durations, in which the circular light-intercepting plate 92 intercepts and transmits the beam signals alternately, are longer thereby to increase the number of beam signals output from the photo-interrupter 98. Contrary, as the revolution rate of the motor 74 is faster for the other portions, the ON/OFF durations are shorter so that the number of output beam signals is reduced. Therefore, the threshold value X is preferably set to be greater for the anterior teeth and smaller for the other portions. As above, after dividing the target portion to be exposed with the X-ray into several sections such as anterior teeth and other portions, the threshold value X may be varied in accordance with sections of the target portion. For example, while defining a set of varying coefficients V for each of sections of the target portion, a set of the threshold values X are obtained by calculating the product of the constant S multiplied with the threshold values X. Thus, the revolving arm 24 may revolve at the constant or varying revolution rate, and also a set of the threshold values X may be defined in accordance with sections of the target portion. As a person skilled in the art easily conceives, the revolution rate may be any rates which can be detected by count values of regular pulses e.g., for speed, moving change, moving phase, and so on.

The combination of the revolution rate of the revolving arm and the threshold value X are conceived as listed below.

Case 1: The revolution rate is fixed and the threshold value X is also fixed.
Case 2: The revolution rate varies and the threshold value X is fixed.
Case 3: The revolution rate is fixed and the threshold value X varies.
Case 4: The revolution rate varies and the threshold value X also varies.

The termination step at Step #5 terminates driving the motor 74 and radiating the X-ray to return to the main routine. While the motor 74 is halted upon determination of the external force on the revolving arm 24, the motor 74 may automatically be rotated in a reverse direction immediately or a predetermined time after stopping the motor.

Figure 17:
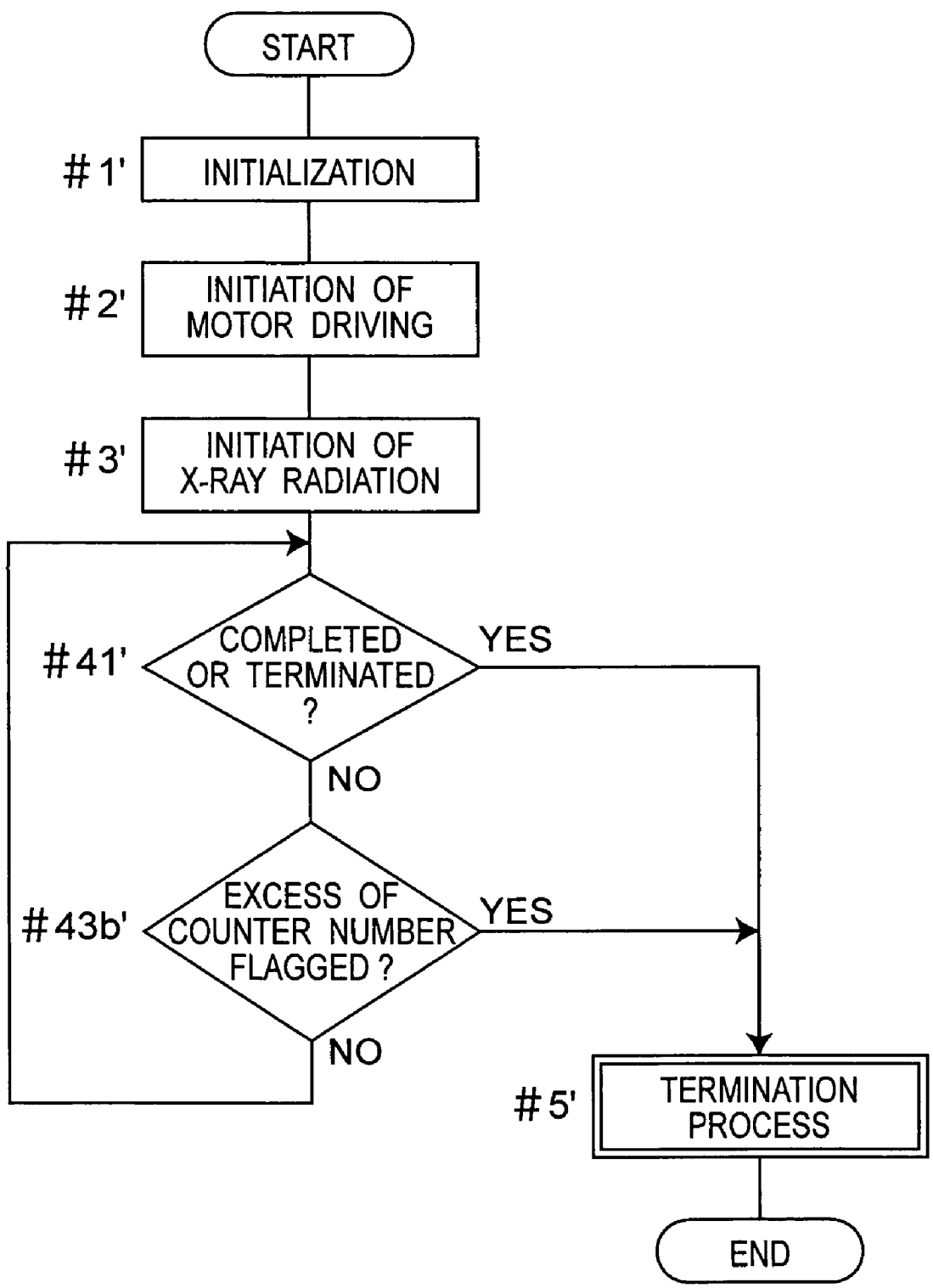
FIG. 17 is a flow chart of the modified control process of FIG. 8.
Figure 18:
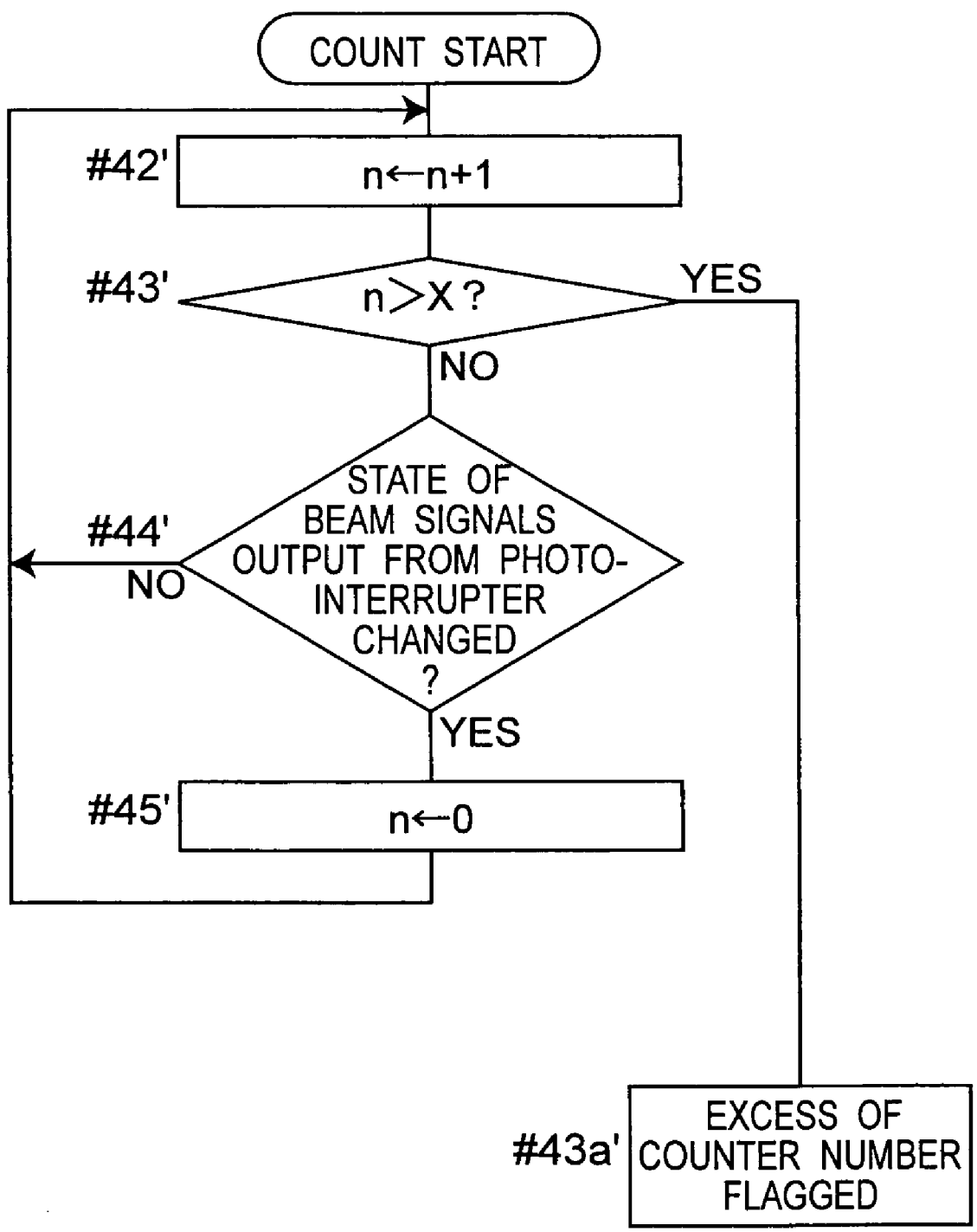
FIG. 18 is a flow chart of the modified control process of FIG. 10.

FIGS. 17 and 18 illustrate a modification of the embodiment shown in FIGS. 8 and 10. The basic flow illustrated in FIGS. 17 and 18 is the same as one of FIGS. 8 and 10 with a couple of exceptions as below. Firstly, only the revolution-failure detecting steps are performed in a sub-routine of FIG. 18 rather than in the main routine of FIG. 17. Also, only if the counter value n exceeds the predetermined value X (in case of "YES" at Step #43'a of FIG. 18) before the states (durations) of the beam signals output from the photo-interrupter 98 has changed, the "count-up" signal or flag is output for showing excess of the counter value n. Meanwhile, the main routine determines, at Step #41', whether the tomography imaging is completed or interrupted, and at Step #43'b of FIG. 17, whether the "count-up" signal is flagged, and the termination step is performed if those conditions met (in cases of "YES" at Step #41' or #43'b of FIG. 17). The remaining features are similar to those previously explained, duplicate description is eliminated. The steps in FIGS. 17 and 18 similar to those in FIGS. 8 and 10 are denoted by the same step numbers with a prime (') According to the modification, for example, when the specifications in the revolution-failure detecting process are altered, only a module performing the sub-routine of FIG. 18 is exchanged so as to readily adapt the new version of the revolution-failure detecting process.

As above, during operation, if the revolving arm 24 is applied with the external force by, for example, the patient's unintentional touch thereon, the X-ray apparatus 10 having the drive change detecting means 90 terminates driving the revolving arm 24 and radiating the X-ray. In particular, the X-ray apparatus 10 detects the drive change of motion of the driving means by detecting the drive change of motion of the member moving synchronously with the driving means. Also, it recognizes the force preventing the motion of the moving means such as the revolving arm 24 when the detected change of the motion (i.e., drive change) exceeds the predetermined value and terminates driving the moving means driven by the driving means and as well as radiating the X-ray. Therefore, in case where the external force (load) is applied to the revolving arm 24 and the driving motor 74 of the revolving arm 24 is terminated, no more process will be continued unless the user gives another instruction to the X-ray apparatus 10. Thus, since the patient's unintentional touches on the revolving arm 24 terminates driving the revolving arm 24 and radiating the X-ray, advantageously and safely, further exposure of the X-ray to the patient is avoided, and any improper X-ray image is prevented so that only a successful X-ray image is used for appropriate diagnosis.

Embodiment 2

Figure 14:
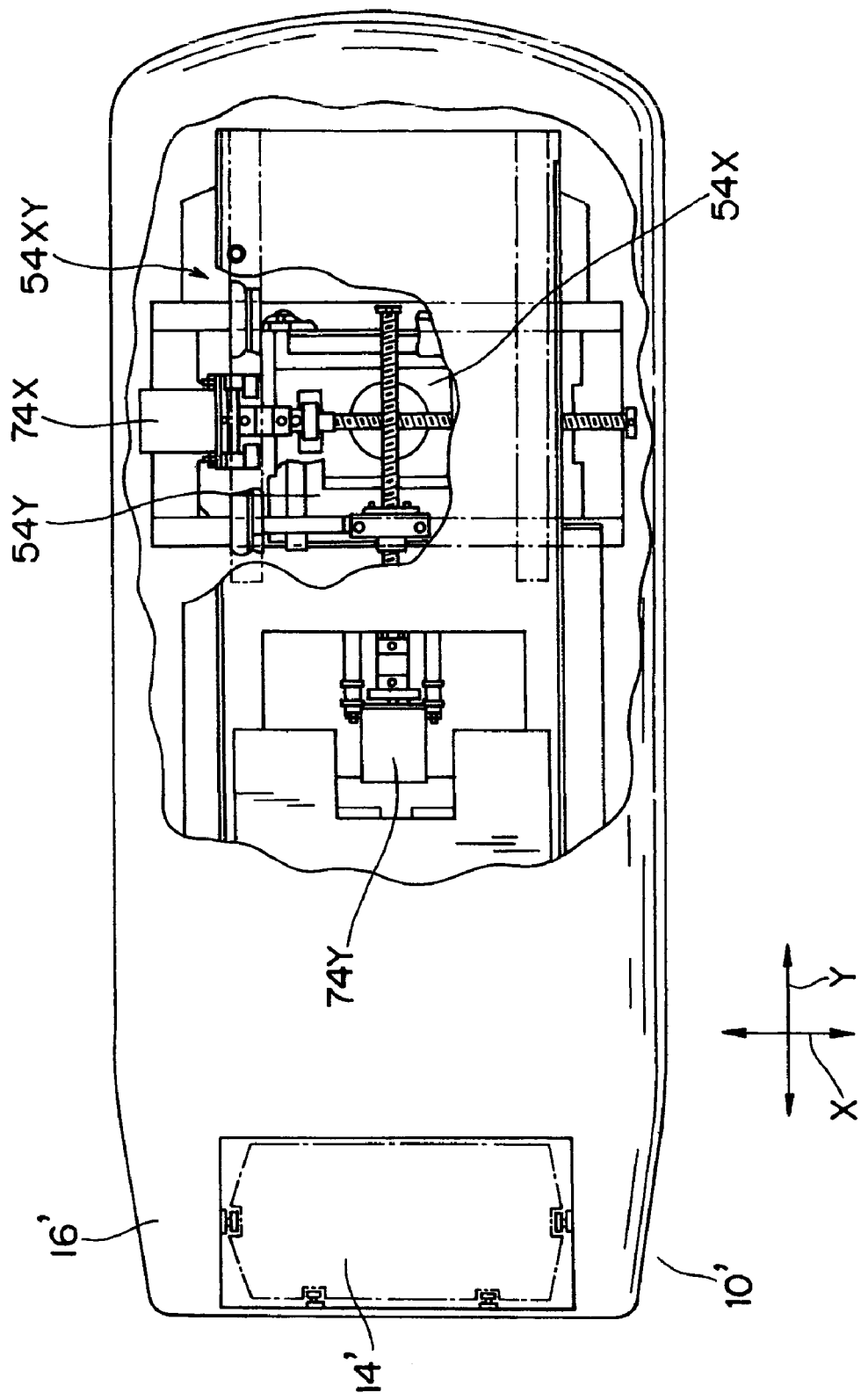
FIG. 14 is a top plan view of the moving mechanism incorporated into the X-ray apparatus according to another embodiment.
Figure 15:
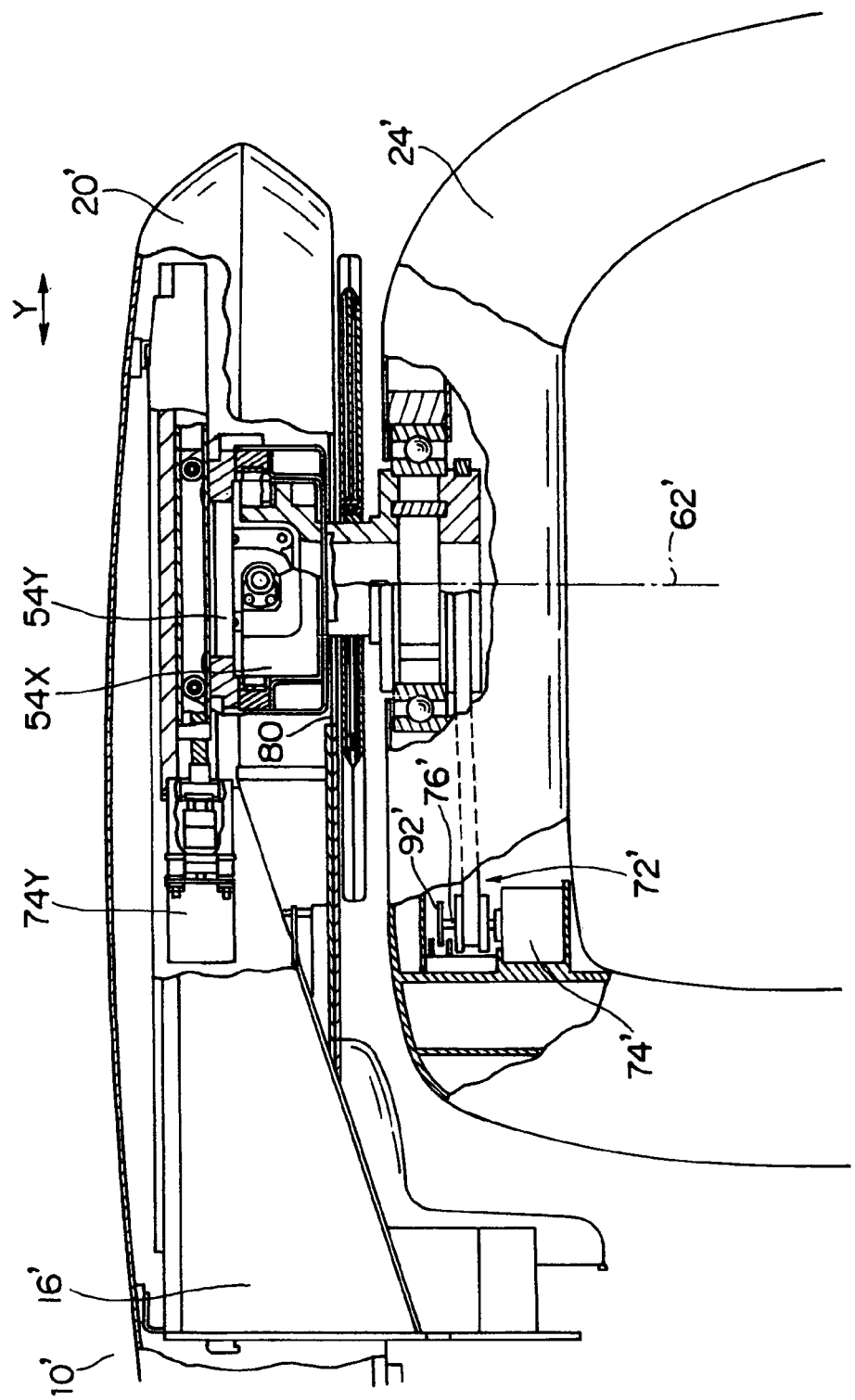
FIG. 15 is a cross sectional view of the moving mechanism of FIG. 14.
Figure 16:
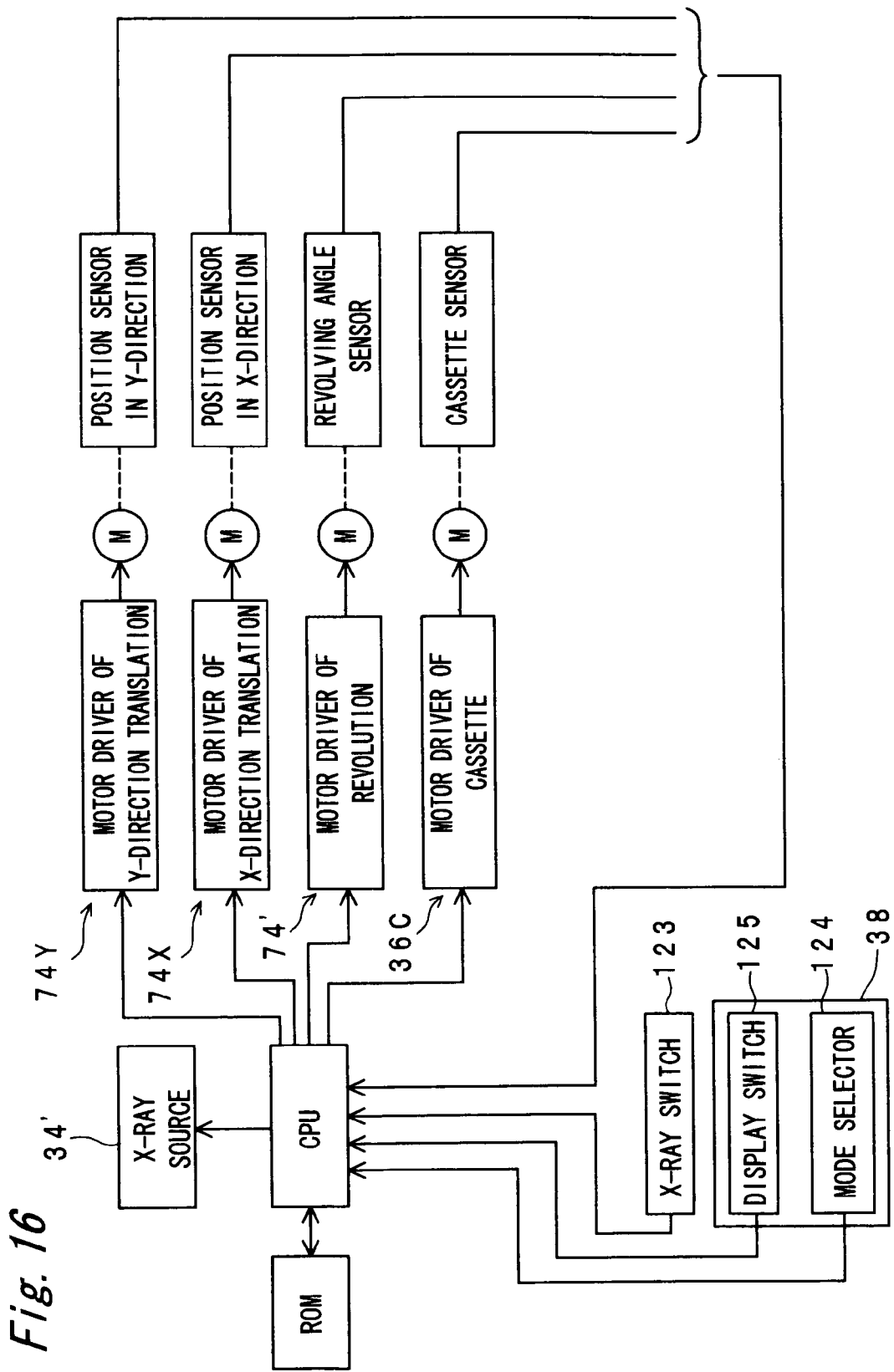
FIG. 16 is a block diagram for controlling the X-ray apparatus of FIG. 14.

The drive change detection as described above can be adapted to the other type of the X-ray apparatus. For example, the X-ray apparatus 10' suggested in the U.S. Pat. No. 6,169,780 B1 can adapt the drive change detection apparatus, which includes a revolution-axis translating mechanism 54XY and a revolution-axis revolving mechanism 72'. As illustrated in FIGS. 14, 15, and 16, the revolution-axis translating mechanism 54XY includes a Y-table 54Y moving forwardly and backwardly (in the Y-direction), an X-table 54X supported on the Y-table 54Y moving transversely (in the X-direction), a Y-direction motor driving device 74Y for driving the Y-table 54Y in the Y-direction, and an X-direction motor driving device 74X for driving the X-table 54X relative to the Y-table in the X-direction. Also, the revolution-axis revolving mechanism 72' includes a revolving motor driving device for revolving the revolving arm 24' around the vertical axis (revolution axis) 62' connecting with the X-table 54X and the revolving arm 24'. In the X-ray apparatus 10', three of those motor driving devices are instructed by a predetermined program to move the revolving arm 24' in both X- and Y-directions as well as to revolve the revolving arm 24' around the revolution axis 62'. Those X- and Y-tables are moving means and the motor driving devices are driving means.

In the X-ray apparatus 10', a rotating member 92' like a circular light-intercepting plate 92 is mounted on the motor rotation of the first embodiment for determining whether the rotation rate of the rotating member 92' falls within the expected range. In particular, when the rotating member 92' serving as a synchronous moving member is influenced with the external force (e.g. contact with the patient), the rotation rate is fluctuated (the drive change is caused), which can be used in cooperation with the same process as the first embodiment for determining whether the rotation rate of the motor is normal. If fluctuation of the rotation rate (i.e., the drive change) exceeds over the predetermined threshold value since the rotating member 92' as a synchronous moving member is influenced with the external force (e.g. contact with the patient), then driving of all of the motors are halted and radiation of the X-ray is stopped immediately. Alternatively, driving of either one of the revolution-axis translating mechanism 54XY and the revolution-axis revolving mechanism 72' may be terminated when the fluctuation of the rotation rate is beyond the given threshold value.

The X-ray apparatus 10' disclosed in the above-referenced U.S. patent includes a cassette driven by the cassette-driving motor driving device 36C for moving horizontally and synchronously with the revolution of the revolving arm. Also, a rotating member may be mounted on the rotation shaft of the cassette-driving motor driving device 36C, and driving of the cassette-driving motor and the above three driving motors may be halted and radiation of the X-ray is terminated once the rotation rate of the motor is reduced less than the predetermined rate by means of the same control process. Instead of the cassette, the same process can be adapted to the X-ray detector for electrically detecting the X-ray. In this case, rather than the cassette-driving motor driving device 36C, operation of an image-data transmitting device for controlling and transmitting the image data is terminated and driving of all of the motors are halted to rotate if the revolving arm 24' receives the external force causing the rotation rate of the rotating member 92' is decreased less than the predetermined value. It should be noted that the photo-interrupter of the X-ray apparatus of the first and second embodiments may use any types of light such as infra-red ray and laser beam.

Other Embodiments

The X-ray apparatuses of the first and second embodiments can be modified in many aspects. In those embodiments, the detecting mechanism for detecting the revolving condition (rate) of the revolving arm includes a rotating plate having a plurality of shielding and transmitting portions, which is mounted on the driving motor of the revolving arm, and a photo-interrupter for detecting beam signals passing through transmitting portions of the rotating plate. However, the rotating plate may be mounted on any members such as gear, pulley, and belt, which rotates synchronously with the rotating shaft of the driving motor other than directly on the driving shaft. Also, while in the first and second embodiments, the arc (or central angle) of the shielding portion of the rotating plate is the same as one of the transmitting portion so that the ON/OFF-durations are the same as each other, the ON-duration may be different from the OFF-duration. Also, either one of ON/OFF-durations is used for determining whether the external force is applied to the revolving arm. Further, in order to detect the rotation status (rate), the photo-interrupter may be replaced with light emitting means provided on the rotating member that moves synchronously with the rotation shaft, and an optical sensor mounted on the stationary member for receiving the beam emitted from the light emitting means. Also, infra-red ray may be emitted and received by an infra-red sensor, or laser beam may be emitted and received by a laser photo-diode. A rotating member having a printed pattern of a bar-code may be driven to rotate synchronously with the driving means, and the bar-code pattern may be read for detecting the rotating status (rate), or a well-known rotary encoder may be used.

Besides, various combinations of the detecting members such as the photo-interrupter and detected members such as the rotating member may be conceived. For example, a synchronous moving member moving synchronously with the rotating-arm driving motor is provided with magnetic bodies arranged at a constant interval along the moving direction, and a magnetic detecting element such as a magnetic sensor, hall element, magnetic semiconductor sensor, and magnetic proximity sensor is positioned adjacent the moving member to detect the revolving state of the revolving arm.

Alternatively, an electronic signal generated by the motor for driving the revolving arm such as a counter-electromotive force signal may be detected by the sensor, for determining that the external force is applied to the revolving arm when the wave of the counter-electromotive force signal or the related electronic signal has the cycle which exceeds a predetermined value therefor.

Further, it is also recognized that the external force is added on the revolving arm by detecting the rotation torque effecting as the load on the rotation shaft of the driving motor of the revolving arm or another rotating member (or rotating shaft) connected with the driving motor, and by determining that the rotation torque is beyond the predetermined range (limit torque or tolerance torque).

Figure 12A:
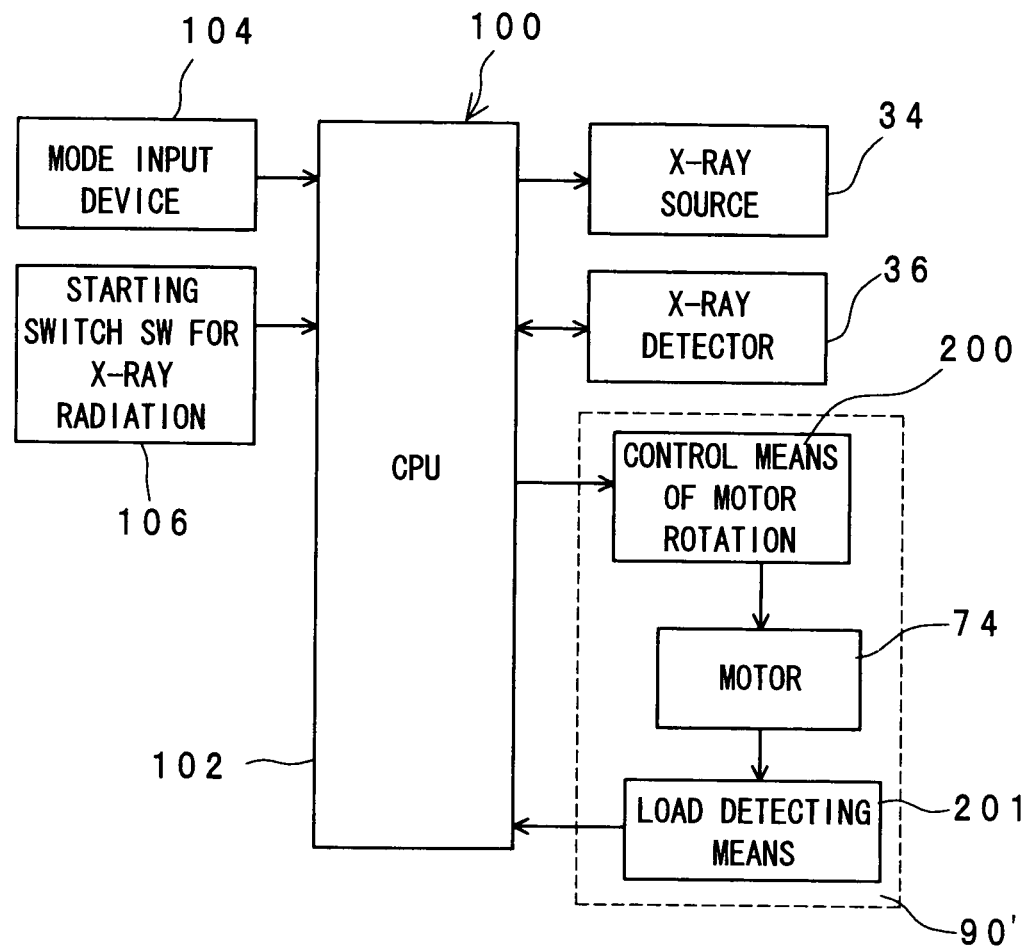
FIG. 12A is a circuit diagram of the revolving-failure detecting apparatus for detecting the rotation torque on the rotation shaft of the motor.
Figure 12B:
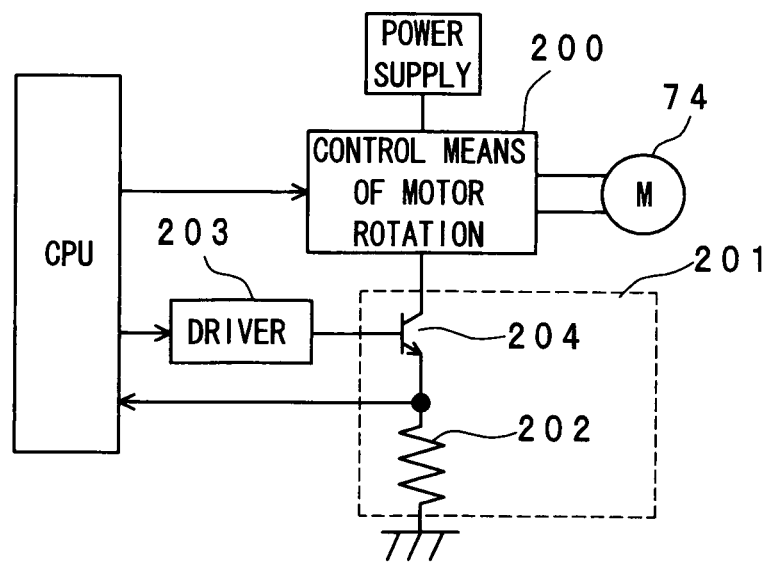
FIG. 12B is an electrical circuit showing an exemplary load detector for detecting the rotation torque.

FIG. 12A illustrates an exemplary control circuit for detecting the rotation torque. While the basic structure for detecting the X-ray by the X-ray detector is similar to that shown in FIG. 7 except the drive change detecting apparatus. According to the architecture of FIG. 12, in the drive change detecting apparatus 90', a load detector 201 detects the rotation torque appearing as the load on the rotation shaft of the driving motor 74 of the revolving arm, and outputs the torque load signal to the CPU 102. The control circuit 100 determines that the external force is added on the revolving arm when the detected torque load is beyond the predetermined threshold value, and terminates driving the motor 74 via the controller 200 for driving the motor. Referring to FIG. 12B showing the electrical circuit of the load detector 201, it includes a driver 203 for driving the motor 74, which receives an instruction from the CPU 102 to switch on or off the transistor switch 204, thereby controlling the rotation of the motor in cooperation with the motor rotation controller 200. The CPU 102 senses the voltage across the resistance 202 connected with the transistor switch 204 for detecting the rotation torque of the motor 74 controlled by the motor rotation controller 200. When it is so determined that the external force is applied to the revolving arm, the CPU 102 may automatically rotates in the reverse direction immediately or some time after termination of driving of the motor, similar to the first embodiment shown in FIG. 7.

Also, while the driving motor (driving force generator for rotation) is provided on the revolving arm in the above embodiments, it may be mounted on the upper frame of the vertical member 16.

The present invention can be applied not only to the panoramic X-ray apparatus but also to the cephalic X-ray apparatus. For example, the commonly assigned Japanese Patent Publication Application No. 2002-17718 discloses an X-ray apparatus usable for both panoramic and cephalic tomography, which is incorporated herein by reference into the present application. The X-ray apparatus includes an X-ray sensor cassette (X-ray detecting means) on one end of an arm used for the cephalic tomography, a X-ray source revolving towards the X-ray sensor cassette during the cephalic tomography imaging, and a cassette holder used for the cephalic tomography (moving means) translating horizontally in response to the revolution of the X-ray source for receiving the X-ray. Similar to the above embodiments, revolution (motion) of the X-ray source and translation (motion) of the X-ray sensor cassette are driven by the motor (driving means). Thus, a rotating plate (not shown) like the circular light-intercepting plate 92 may be mounted on the rotating shaft of the motor or rotating member rotating synchronously with the motor for detecting that the external force is applied with the X-ray source or the X-ray sensor cassette (with e.g., touch with the patient) by the same process as described above when the rotation state (rate) is beyond the predetermined value (e.g., drive change). If so determined, the motor can be halted to drive and the X-ray can be terminated to radiate.

The above Japanese patent publication also discloses the X-ray source fixed in the cephalic radiography imaging and a secondary slit member (moving means) having a secondary slit (limiting means of X-ray beam width), which translates horizontally for receiving the X-ray. As the secondary slit member is driven by also a motor, on which the rotating member may be mounted for detecting the rotation status (rate) of the motor. Then, the same process can be adapted for control the secondary slit member and the motor as well.

Further, the present invention can be used also in the conventional X-ray apparatus using an X-ray film cassette. The panoramic tomography requires the film to be rolled in accordance with sections of the target portion, which is driven generally by the motor. Similarly, the rotating member like the circular light-intercepting plate 92 may be mounted on the motor rotating shaft or the rotating element rotating synchronously with the motor for detecting the rotation status (rate) of the motor. Then, the same process can be used for control the secondary slit member and the motor as well.

In the plane tomography, a person being tested is positioned between the X-ray source and the X-ray detector opposing each other, which move in opposite direction. Also, the rotating member like the circular light-intercepting plate 92 may be mounted on the motor rotating shaft or the rotating element rotating synchronously with the motor for detecting the rotation status (rate) of the motor, thereby controlling the X-ray source and the X-ray detector in accordance with the similar process.

What is claimed is:

1. An X-ray apparatus comprising:
   a fixed frame having first and second guide members;
   a translating frame supported by the first guide member, capable of being translated relative to the fixed frame along a predetermined direction;
   a revolving arm supported by the translating frame, capable of revolving around a vertical revolution axis;
   a guide plate secured on the second guide member of the fixed frame;
   a driving mechanism for revolving the revolving arm around the vertical revolution axis;
   a clock pulse generator for generating clock pulse signals;
   drive change detecting means for detecting the clock pulse signals in ON/OFF durations which appear alternately and synchronously with the driving of the driving mechanism so as to detect the amount of the drive change of the driving mechanism;
   the revolving arm having a vertical rod provided at an eccentric position spaced from the vertical revolution axis by a predetermined distance; and
   the guide plate having a guide slot extending in a direction substantially traverse to the predetermined direction, for receiving the vertical rod therethrough;
   wherein revolution of the revolving arm around the vertical revolution axis causes the vertical rod to move along the guide slot, thereby horizontally translating the revolving arm relative to the fixed frame; and
   wherein revolution of the revolving arm by the driving mechanism is terminated when the amount of the drive change is beyond a predetermined range of threshold values.

2. The X-ray apparatus according to claim 1, wherein the X-ray apparatus is a dental panoramic X-ray apparatus.

3. The X-ray apparatus according to claim 1, wherein the guide slot is substantially V-shaped.

4. The X-ray apparatus according to claim 1,
   wherein the revolving arm including a first suspending portion provided with an X-ray source radiating an X-ray, and a second suspending portion provided with an X-ray detector detecting the X-ray from the X-ray source, and
   wherein the driving mechanism revolves the revolving arm around the vertical revolution axis so as to keep the X-ray source and the X-ray detector opposing to each other.

5. The X-ray apparatus according to claim 1,
   the driving mechanism including a motor for revolving the revolving arm around the vertical revolution axis;
   a moving member provided on a rotating shaft of the motor synchronously moving therewith; and
   a drive change detecting means for detecting drive change of the motor by detecting drive change of the moving member;
   wherein the motor is deactivated if rotation of the motor is detected as not being normal based upon the drive change of the motor.

6. The X-ray apparatus according to claim 5, wherein the motor is a stepping motor.

7. The X-ray apparatus according to claim 1, wherein radiation of the X-ray is terminated when the revolving arm is applied with the external force preventing motion thereof.

8. The X-ray apparatus according to claim 1,
   wherein the drive change detecting means compares a counter number of the clock pulse signals with a threshold value and determines as being abnormal if the counter number is beyond the threshold value, and
   wherein the threshold value is set to be greater when a panoramic tomography is imaged for anterior teeth than those for the other portions.

* * * * *